United States Patent [19]

Hoenig

[11] 4,117,715
[45] Oct. 3, 1978

[54] APPARATUS FOR MEASURING CHARGE ON, AND DENSITY OF, AIRBORNE PARTICULATES

[75] Inventor: Stuart A. Hoenig, Tucson, Ariz.

[73] Assignee: Ransburg Corporation, Indianapolis, Ind.

[21] Appl. No.: 812,713

[22] Filed: Jul. 5, 1977

[51] Int. Cl.² .................. G01N 31/00; G01R 5/28
[52] U.S. Cl. ........................................... 73/28; 324/32
[58] Field of Search ............ 73/28, 61, 32 R, 432 PS; 324/32, 109; 55/270, 103, 104, 105

[56] References Cited

U.S. PATENT DOCUMENTS

| 1,517,144 | 11/1924 | Anderson | 73/28 |
| 2,129,527 | 9/1938 | Fassin | 73/28 |
| 3,605,485 | 9/1971 | Badzioch et al. | 73/28 |
| 3,753,102 | 8/1973 | Beck | 324/32 |

FOREIGN PATENT DOCUMENTS

| 1,170,047 | 11/1969 | United Kingdom | 73/28 |
| 197,271 | 7/1967 | U.S.S.R. | 73/28 |

Primary Examiner—Stephen A. Kreitman
Attorney, Agent, or Firm—Merrill N. Johnson; Richard D. Conard

[57] ABSTRACT

A simple, inexpensive, hand-held and operated apparatus for providing a substantially immediate indication of the density of, and charge on, airborne particulate contaminants of a predetermined size or within a predetermined size range includes a first filter for removing particulate contaminants having a size greater than the maximum size of the range, and a second filter for passing all particulate contaminants having size smaller than the minimum size of the range. The two filters are arranged in series in a housing, and a hand-operated pump having a known capacity is used to draw contaminant-laden air through the series filters. A conductive screen is placed against the second filter to provide an electrical indication of the polarity of the charge on the contaminants trapped by the second filter.

17 Claims, 4 Drawing Figures

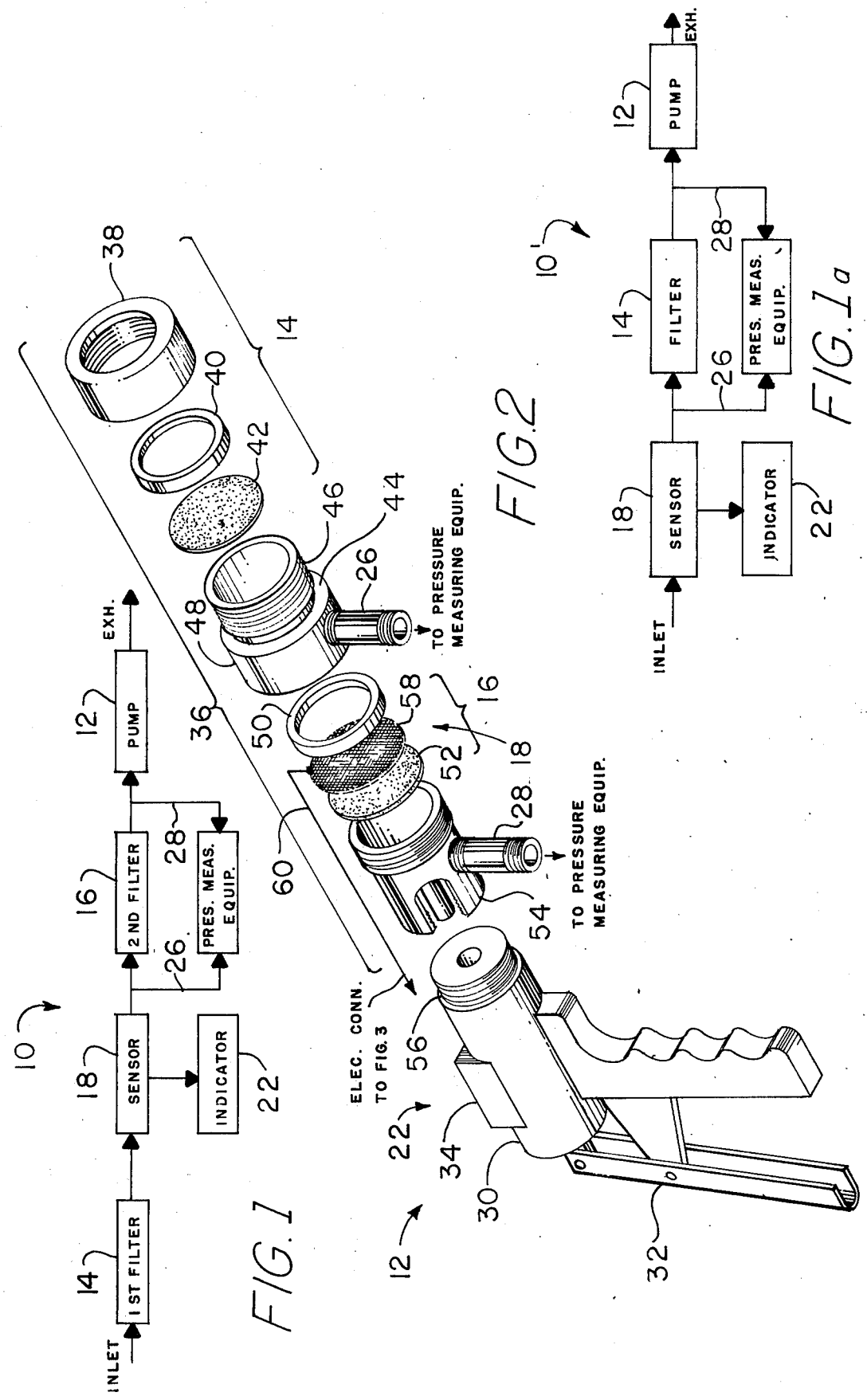

APPARATUS FOR MEASURING CHARGE ON, AND DENSITY OF, AIRBORNE PARTICULATES

This invention relates to an apparatus for determining the charge on, and the density of, airborne particulate contaminants. Particularly, this invention relates to a simple apparatus providing a direct determination of these parameters for pollutants in a work environment.

Many types of apparatus for determining the electrostatic charge in a flowing stream of material are known. There is, for example, the apparatus described in Beck, U.S. Pat. No. 3,753,102. There are also various types of apparatus for determining, either directly or indirectly the density of particulate contaminants in an atmosphere, such as the air in a work area. Illustrative of such apparatus is that described in Peck, U.S. Pat. No. 3,295,359. This apparatus, however, contemplates a very direct determination of the amounts and types of various contaminants in the air. The technique outlined in the Peck patent includes removing from the apparatus the filters used to filter contaminant particles from the air stream and examining them under a microscope. This, of course, is a time-consuming and tedious method which cannot yield any immediate information regarding the density of the contaminants suspended in the atmosphere. Badzioch et al, U.S. Pat. No. 3,605,485 discloses generally two methods for determining the concentration of particulate contaminants in a gas stream. The first of these is by maintaining constant pressure differential across a filter element, and allowing the flow rate through the filter element to vary. Alternatively, Badzioch et al suggests maintaining a constant flow rate through the filter element while variations in the pressure differential across the filter element are monitored.

It is a primary object of the present invention to provide a simple, inexpensive, hand-operated and held apparatus for providing a substantially immediate indication of the density of, and charge on, airborne particulate contaminants. In accordance with an illustrative embodiment of the instant invention, the airborne particulate contaminants analyzed can be selected to fall within a predetermined size range. That is, the analysis with the apparatus of the instant invention can be performed upon particulate contaminants which are: greater than a predetermined size; less than a first predetermined size and greater than a second predetermined size; or, less than a predetermined size. This feature provides maximum flexibility of particulate contaminant analyzing apparatus.

According to the invention, an apparatus for measuring the charge on, and density of, airborne particulate contaminants includes means for providing a predetermined flow rate of contaminant-laden gas, means for sensing the charge on the particulate contaminants in the flow reaching the sensing means and for providing an indication of the sensed charge, and means for measuring the density of particulate contaminants reaching the sensing means at the predetermined flow rate and for providing an indication of such density.

In the illustrative embodiment, the apparatus further includes first means for filtering contaminant particles greater than a predetermined size from the flow, the first filter means being located upstream from the sensing means in the flow path. The illustrative apparatus comprises second filter means including an electrically conductive element for contacting particles within a predetermined size range to produce on the conductive element an electrical indication of the polarity of the charge on the particulate contaminants within such size range.

Further according to the illustrative embodiment, the density-measuring means includes means for sensing the pressure drop across the second filter means, and the means for providing an indication of the density of particulate contaminants within the predetermined size range comprises means for providing an indication of such pressure drop. This includes first and second pressure taps, the first tap located upstream in the particulate contaminant flow path from the second filter means, and the second tap located downstream therefrom.

In an illustrative embodiment, the means for providing a predetermined flow rate through the apparatus comprises a hand-operated pump for drawing a predetermined volume of contaminant-laden gas per pump stroke.

Further according to the illustrative embodiment, the means for providing an indication of the polarity of the sensed charge includes circuit means coupled to the sensing means for sensing the polarity of the charge, and first and second visual indicators. The first indicator indicates the presence of a positive charge on the sensing means, and the second indicator indicates the presence of a negative charge on the sensing means.

The invention may best be understood by referring to the following detailed description and accompanying drawings which illustrate the invention. In the drawings:

FIG. 1 is a block diagram showing a system set up according to the present invention;

FIG. 1a is a block diagram showing an alternative system set up according to the present invention;

FIG. 2 is an exploded perspective view of an apparatus constructed according to the present invention; and, FIG. 3 is a partly block and partly schematic diagram of an electric circuit useful in the present invention.

Figure 3:
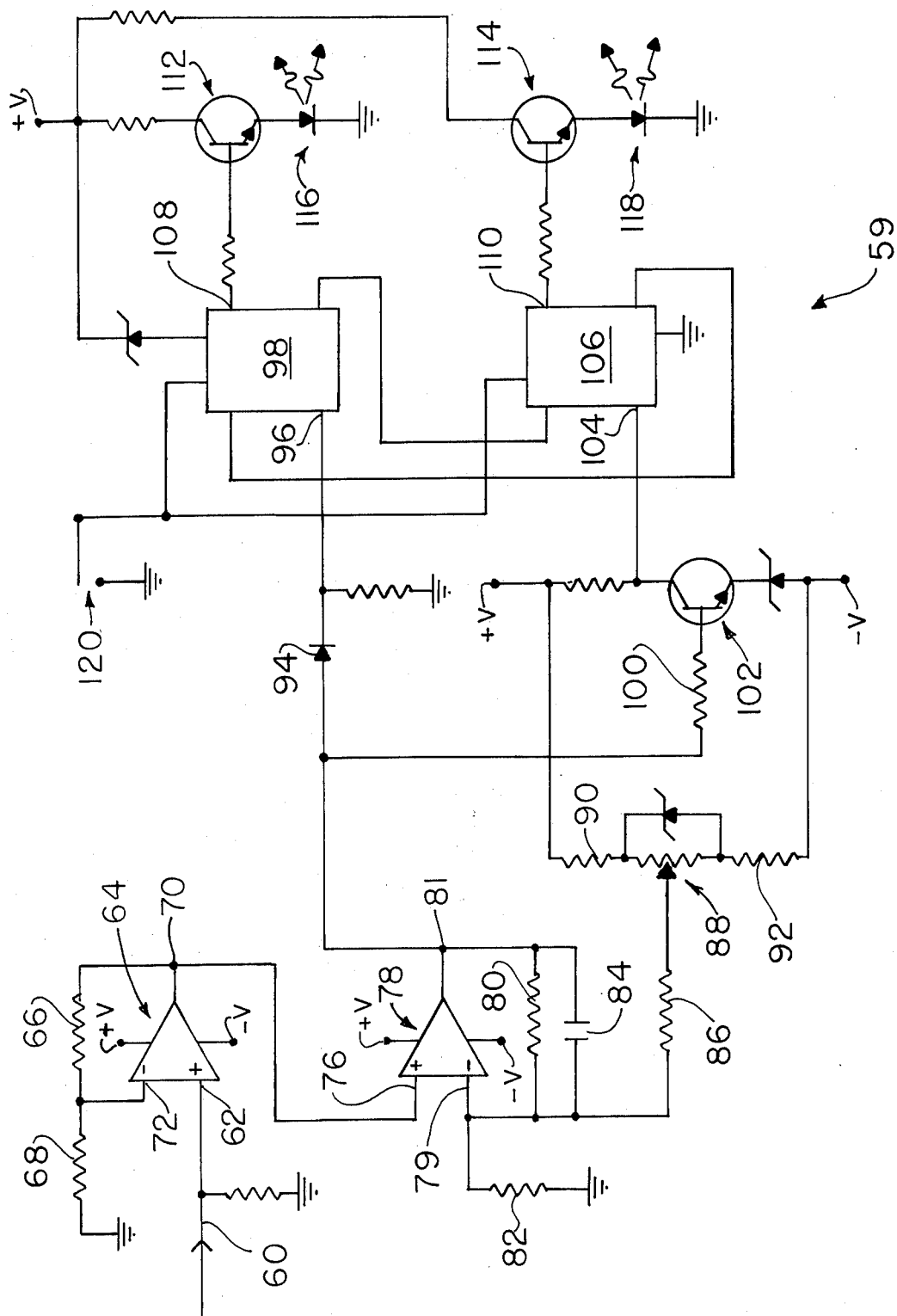

Referring now particularly to FIG. 1, contaminant-laden air from, for example, within a mine, is pulled through the apparatus 10 by hand-actuation of a pump 12. Pump 12 draws a constant volume of air with each pump stroke through a first filter 14, past a charge sensor 18, and through a second filter 16. The air is then exhausted through the pump 12. Optionally, and as illustrated in FIG. 1a, the air is drawn past charge sensor 18 into the first filter 14 and then exhausted through the pump 12. An indicator 22 is coupled to sensor 18 to provide a visual indicator of the polarity of the charge sensed thereby. In the embodiment of FIG. 1, a first pressure tap 26 is provided in the line upstream from second filter 16. A second pressure tap 28 is provided in the line downstream from filter 16. In the embodiment of FIG. 1a, pressure tap 26 is provided upstream from filter 14 and pressure tap 28 is provided downstream therefrom.

In operation of the apparatus 10 of FIG. 1, the first filter 14 removes all contaminant particles having diameters greater than or equal to a first size S1 from the air flowing through the apparatus. Filter 14 can have a selectively variable filter element to block the passage of any contaminant particles of, for example, greater than respirable size. From filter 14, the air drawn through apparatus 10 flows through second filter 16 which blocks the passage of all particles having size greater than or equal to a size S2. Filter 16, like filter 14, can have a filter element which is selectively variable so that filter 16 can block all respirable particles having sizes larger than, for example 0.6 micron.

Sensor 18 is attached to the upstream side of second filter 16. Sensor 18 senses the charge on any particle which is blocked by filter 16. Signals relative to the polarity of the charge blocked by filter 16 are conveyed from sensor 18 to indicator 22 to produce a visual indication of the polarity of the charge on the particles removed from the air stream by filter 16. In the embodiment of FIG. 1a, sensor 18 of apparatus 10' senses the polarity of the charge on all particles trapped by the single filter 14. The filter 14 can be of a variable size so that the charges on various size "fractions" of the total contaminant mass in an atmosphere can be selectively examined. The polarity of particulate contaminants has been shown under many circumstances to depend in part upon the size of the particulate contaminants (see, for example, Stuart A. Hoenig, Charles R. Russ and Joseph B. Bidwell, APPLICATION OF ELECTROSTATIC FOG TECHNIQUES TO THE CONTROL OF RESPIRATORY PARTICULATES, May 1, 1976, Department of Electrical Engineering, University of Arizona, Tuscon, Ariz. 86721). Thus, it may be beneficial to determine the polarity of the charge on the particulate contaminants filtered from the flowing air stream by filter 14. Placing sensor 18 upstream from filter 14 as illustrated in FIG. 1a will achieve this additional function.

Turning now to FIG. 2, there is illustrated a quite simple and inexpensive apparatus of the type illustrated diagrammatically in FIG. 1. The pump 12 of this apparatus includes a housing 30 providing a hand grip, and handle 32 which can be grasped for hand operation. Housing 30 is generally cylindrical and includes a portion 34 which houses the necessary electronic circuitry, including battery power supplies, for the apparatus. Pump 12 draws a constant volume of contaminant-laden air with each pump stroke. In the illustrated embodiment, that volume was 0.015 liter.

A filter and sensor housing 36 is attached to the front end of pump housing 30. Housing 36 includes an internally threaded retainer collar 38, a sealing and mounting ring 40 and a coarse filter element 42 which constitute first filter 14. A collar 44 has a reduced diameter, externally threaded forward section 46, onto which is threaded retainer collar 38. Ring 40 and filter element 42 are thereby captured between collar 38 and collar 44. Collar 44 also includes a larger diameter, internally threaded rearward portion 48. Portion 48 is designed to receive a sealing ring 50 and fine mesh filter element 52 (second filter 16) which are retained therein by an attachment collar 54. Collar 54 is externally threaded at its forward end to be received in section 48 of collar 44. Collar 54 is internally threaded at its rearward end to receive the externally threaded front portion 56 of housing 30.

A conductive metal screen 58 is mounted between ring 50 and filter element 52. Ring 50 presses this screen 58 against the front surface of filter element 52. Thus, contaminant particles which passed through filter element 42, but are trapped on the upstream surface of filter element 52 can transfer their charge to conductive screen 58. Screen 58 is insulated from the other metal parts of the apparatus 10 by ring 50 and filter element 52. A conductor 60 extends from screen 58 through the wall of collar 44 to housing portion 34 the pump 12. Conductor 60 conveys information related to the polarity of the charge on the particles removed from the stream of air flowing through filter element 52 to electronic circuits in housing portion 34.

Pressure tap 26 is provided in the large section 48 of collar 44. This tap conveys information related to the pressure upstream from filter 16 to suitable pressure measuring equipment (shown diagrammatically). Pressure tap 28 is provided in attachment collar 54 downstream from filter 16. Tap 28 is also coupled to the pressure measuring equipment. The difference between the pressure at tap 26 and the pressure at tap 28 is the pressure drop across filter 16. Since screen 58 is a relatively open mesh screen, it does not contribute to the pressure drop across filter 16. The filter apparatus illustrated in FIG. 2 is based upon a commercial filter and housing mechanism available from Nuclepore Corporation of Pleasanton, Calif. The pressure measuring equipment is available from Statham Instruments, Inc., of Oxnard, Calif.

In the embodiment of the invention constructed, filter 14 was chosen to have a mesh sufficient to stop all particles larger than 8 microns in diameter, while filter 16 was chosen to remove all particles larger than 0.6 micron in diameter. Screen 58 was a 100 mesh copper screen. Pump 12 can be any of a number of commercially available devices. One which provided satisfactory results was available from Nalgene Division of Nalge Company of Rochester, N.Y.

As the cake of contaminant particles builds up on screen 58, the difference between the pressure readings at taps 26, 28 will increase. From information currently available from Nuclepore Corporation, it has been determined that, at least during the early stages of filter 16 capture of contaminant particles, the change in pressure drop is linear with particle cake thickness. Thus, the operator need only empirically establish a table or graph of dust cake thickness as a function of pressure drop between taps 26, 28 to determine the dust cake thickness on filter element 52 after a predetermined volume of contaminant-laden air has been drawn through pump 12. Since the exposed area of filter element 52 is known, the dust cake thickness can be multiplied by the exposed area of filter element 52 to determine the volume of contaminant particles trapped in filter element 52 after a predetermined volume of air has been drawn through pump 12. These figures will yield the density of particulate contaminants of such size that they were not removed by filter element 42 (filter 14) but were removed by filter element 52 (filter 16).

With a system of the type illustrated, density and polarity of charge of particulate contaminants in an atmosphere, and particularly of particulate contaminants less than a predetermined size, greater than a predetermined size, or between two predetermined sizes, can readily be determined. These data can be obtained without the necessity of any complex weighing or observation of filter elements, and without any heavy, or complex mechanical pumping apparatus. This apparatus is extremely versatile.

Turning now to FIG. 3, an electric circuit 59 which is useful with the instant invention, and which can be housed in housing portion 34 is illustrated. In this apparatus, conductor 60 is connected to the non-inverting input terminal 62 of an amplifier 64. Suitable resistors 66, 68 provided feedback between the output terminal 70 of amplifier 64 and the inverting input terminal 72 thereof. The terminal 70 is also coupled to the input terminal 76 of an amplifier 78. The feedback and coupling of amplifier 78 to the subsequent stages are provided by a network comprising resistors 80, 82 and capacitor 84. The inverting input terminal 79 of amplifier 78 is balanced through the network comprising resistor 86 and the series combination of potentiometer 88 with resistors 90, 92 between positive and negative low potential supplies +V and −V, respectively.

Output terminal 81 of amplifier 78 is coupled through a diode 94 to an input terminal 96 of a waveshaping integrated circuit 98. Output terminal 81 is also coupled through a resistor 100 to the base of an inverting amplifier transistor 102. The collector of transistor 102 is coupled to the input terminal 104 of a waveshaping integrated circuit 106. The output terminals 108, 110, of waveshaping integrated circuits 98, 106, respectively, are coupled to driver transistors 112, 114, respectively. Light emitting diodes (LED's) 116, 118, respectively, in the emitter circuits of transistors 112, 114, respectively, are responsive to conduction by transistors 112, 114. Energization of LED 116 indicates that the polarity of the potential on screen 58 is positive. Energization of LED 118 indicates that the polarity of the potential on screen 58 is negative. A switch 120 is closed momentarily to return the circuit 59 to its initial state for a subsequent measurement.

It is to be understood that a meter could be provided in lieu of, or in addition to, the circuitry of FIG. 3, to provide a numerical readout proportional to the charge on screen 58.

What is claimed is:

1. Apparatus for measuring the density of, and charge on, particulate contaminants suspended in a gas comprising means for providing a predetermined flow rate of contaminant-laden gas, means for sensing the charge on the particulate contaminants in the flow reaching the sensing means and for providing an indication of the sensed charge, the sensing means including filter means having an electrically conductive element for contacting particles within a predetermined size range to produce on the electrically conductive element an electrical indication of the polarity of the charge on the particulate contaminants within such size range, and means for measuring the density of particulate contaminants reaching the sensing means at the predetermined flow rate and for providing an indication of such density.

2. The apparatus of claim 1 and further including additional means for filtering contaminant particles greater than a predetermined size from the flow.

3. The apparatus of claim 1 wherein the density-measuring means includes means for sensing the pressure drop across the filter means, and the means for providing an indication of the density of particulate contaminants within the predetermined size range comprises means for providing an indication of such pressure drop.

4. The apparatus of claim 3 wherein the means for sensing the pressure drop across the filter means comprises first and second pressure taps, the first tap being located upstream in the particulate contaminant flow path from the filter means and the second tap being located downstream therefrom.

5. The apparatus of claim 1 wherein the means for providing a predetermined flow rate through the apparatus comprises a hand-held and hand-operated pump for drawing a predetermined volume of contaminant-laden gas per pump stroke.

6. The apparatus of claim 1 and further including additional means for filtering particulate contaminants greater than a first predetermined size from the flow, the additional filter means being located upstream from the sensing means in the flow path.

7. The apparatus of claim 6 wherein the first-mentioned filter means includes a second filter for filtering particulate contaminants greater than a second predetermined size from the flow, the second filter being located downstream from the additional filter means and the electrically conductive element in the flow path.

8. Apparatus for measuring the density of, and charge on, particulate contaminants suspended in a gas comprising means for providing a predetermined flow rate of contaminant-laden gas, means for sensing the charge on the particulate contaminants in the flow reaching the sensing means and for providing an indication of the sensed charge, and means for measuring the density of particulate contaminants reaching the sensing means at the predetermined flow rate and for providing an indication of such density, the means for providing an indication of the sensed charge including electric circuit means coupled to the sensing means for sensing the polarity of the charge and first and second indicators, the first for indicating the presence of a positive charge on the sensing means, and the second for indicating a negative charge on the sensing means.

9. Apparatus for measuring the density of, and charge on, particulate contaminants suspended in a gas comprising means for providing a predetermined flow rate of contaminant-laden gas, means for sensing the charge on the particulate contaminants in the flow reaching the sensing means and for providing an indication of the sensed charge, means for measuring the density of particulate contaminants reaching the sensing means at the predetermined flow rate and for providing an indication of such density, first means for filtering particulate contaminants greater than a first predetermined size from the flow, the first filter means being located upstream from the sensing means in the flow path, and second means for filtering particulate contaminants greater than a second predetermined size from the flow, the second filter means being located downstream from the first filter means and the sensing means in the flow path, the sensing means including a conductive screen mounted upstream in the flow path from the second filter means.

10. The apparatus of claim 9 and further including means for housing and supporting the first filter means and second filter means in spaced-apart relation with the conductive screen therebetween.

11. The apparatus of claim 10 wherein the density measuring means includes first and second pressure taps provided in the housing means for measuring the pressure on the upstream and down stream sides, respectively, of the second filter means.

12. The apparatus of claim 11 wherein the flow-providing means includes a hand-held and operated pump for drawing a predetermined volume of contaminant-laden gas per pump stroke.

13. Apparatus for measuring the charge on particulate contaminants entrained in a gas comprising a pump for creating a predetermined flow rate of contaminant-laden gas, first means for filtering contaminant particles greater than a first predetermined size from the gas flow and means for sensing the polarity of the charge on the contaminant particles filtered by the first filter means, and a housing for supporting the first filter means and the sensing means, the housing being connected to the pump to induce gas flow through the housing, the sensing means comprising a screen of conductive material located upstream in the flow path from the first filter means to sense the polarity of contaminant particles greater than the first predetermined size.

14. The apparatus of claim 13 and further comprising second means for filtering particles greater than a second predetermined size from the gas flow, the second filter means being located upstream from the sensing means in the gas flow path, the second filter means being supported by the housing.

15. The apparatus of claim 14 and further including electric circuit means for providing an indication of the polarity of the sensed charge, the electric circuit means being coupled to the sensing means.

16. The apparatus of claim 14 wherein the housing further includes means for measuring the density of particulate contaminants filtered from the flow by the first filter means.

17. The apparatus of claim 16 wherein the density measuring means includes first and second gas pressure taps provided on the housing, the first tap opening interiorly of the housing upstream from the filter means in the gas flow path, and the second tap opening interiorly of the housing downstream from the first filter means in the gas flow path, the pressure differential across the first filter means being indicative of the thickness of the deposit of contaminant particles on the first filter means.

* * * * *